US011857570B2

(12) United States Patent
Papa et al.

(10) Patent No.: US 11,857,570 B2
(45) Date of Patent: *Jan. 2, 2024

(54) NATURAL COMPOSITION FOR USE IN GYNECOLOGY

(71) Applicant: Organicare LLC, Austin, TX (US)

(72) Inventors: Franco Papa, Lesa (IT); Renato Colognato, Ispra (IT)

(73) Assignee: ORGANICARE LLC, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/827,504

(22) Filed: May 27, 2022

(65) Prior Publication Data
US 2022/0362288 A1 Nov. 17, 2022

Related U.S. Application Data

(63) Continuation of application No. 16/500,926, filed as application No. PCT/IB2018/052324 on Apr. 4, 2018, now Pat. No. 11,369,632.

(30) Foreign Application Priority Data

Apr. 5, 2017 (IT) .................. 102017000037319

(51) Int. Cl.
A61K 33/40 (2006.01)
A61P 15/02 (2006.01)
A61P 31/04 (2006.01)
A61P 31/10 (2006.01)
A61K 9/00 (2006.01)
A61K 36/53 (2006.01)
A61K 36/537 (2006.01)
A61K 36/54 (2006.01)
A61K 36/61 (2006.01)
A61K 36/68 (2006.01)
A61K 36/88 (2006.01)
A61K 36/886 (2006.01)
A61K 36/9066 (2006.01)
A61K 36/9068 (2006.01)
A61K 47/44 (2017.01)

(52) U.S. Cl.
CPC ............ *A61K 33/40* (2013.01); *A61K 9/0014* (2013.01); *A61K 36/53* (2013.01); *A61K 36/537* (2013.01); *A61K 36/54* (2013.01); *A61K 36/61* (2013.01); *A61K 36/68* (2013.01); *A61K 36/88* (2013.01); *A61K 36/886* (2013.01); *A61K 36/9066* (2013.01); *A61K 36/9068* (2013.01); *A61K 47/44* (2013.01); *A61P 15/02* (2018.01); *A61P 31/04* (2018.01); *A61P 31/10* (2018.01)

(58) Field of Classification Search
CPC ...... A61K 33/40; A61K 36/53; A61K 36/537; A61K 36/54; A61K 36/61; A61K 36/68; A61K 36/88; A61K 36/9066; A61K 36/9068; A61K 47/44; A61K 9/0014; A61P 15/02; A61P 31/04; A61P 31/10
See application file for complete search history.

(56) References Cited

U.S. PATENT DOCUMENTS

| | | | |
|---|---|---|---|
| 4,185,025 A | 1/1980 | Carduck et al. | |
| 5,997,876 A | 12/1999 | Shikhashvili et al. | |
| 11,369,632 B2* | 6/2022 | Papa | A61K 36/63 |
| 2005/0008663 A1 | 1/2005 | Lerma | |
| 2005/0010069 A1 | 1/2005 | Fitchett | |
| 2006/0074129 A1 | 4/2006 | Mirabal et al. | |
| 2008/0045594 A1 | 2/2008 | Piccirilli et al. | |
| 2009/0291122 A1 | 11/2009 | Vandeputte | |
| 2013/0237933 A1 | 9/2013 | Ko | |
| 2014/0287064 A1* | 9/2014 | Swenholt | A61K 45/06 424/665 |
| 2016/0106128 A1* | 4/2016 | Musco | A61K 8/9789 426/640 |

FOREIGN PATENT DOCUMENTS

| | | | | |
|---|---|---|---|---|
| CN | 1411857 A | 4/2003 | | |
| EP | 2014295 | 1/2009 | | |
| EP | 2014295 A2 * | 1/2009 | ........... | A61K 36/185 |
| EP | 2510912 | 10/2012 | | |
| JP | 2001-524501 A | 12/2001 | | |
| JP | 2005-112796 A | 4/2005 | | |
| JP | 2005-112798 A | 4/2005 | | |
| JP | 2005-139176 A | 6/2005 | | |
| JP | 2012-504710 A | 2/2012 | | |
| KR | 10-0414639 B1 | 1/2004 | | |
| KR | 10-2016-0137797 A | 12/2016 | | |
| WO | 2010128906 A1 | 11/2010 | | |
| WO | WO-2010128906 A1 * | 11/2010 | ......... | A61F 13/8405 |

(Continued)

OTHER PUBLICATIONS

Kim et al. "*Candida albicans*, A Major Human Fungal Pathogen" in the Journal of Microbiology (2011), vol. 49, No. 2, pp. 171-177 (Year: 2010).*
Petersen Braun et al. (WO 2008148572 A1, using Eng. Trans.) (Year: 2008).*
Geweely, Naveen S.I., Antifungal Activity of Ozonized Olive Oil (Oleozone); International Journal of Agreiculture & Biology; vol. 8, No. 5, 2006; 6 pgs.
Japanese Office Action; Application No. 2020-504464; dated Apr. 5, 2022; 12 pages.
Almeida, et al., "Ozonized Vegetable Oils and Therapeutic Properties: A Review". Orbital, The Electronic Journal of Chemistry, vol. 4, No. 4, Oct.-Dec. 2012, pp. 313-326.

(Continued)

*Primary Examiner* — Blessing M Fubara
(74) *Attorney, Agent, or Firm* — Kowert, Hood, Munyon, Rankin & Goetzel, P.C.

(57) ABSTRACT

The present invention relates to a composition based on components of natural origin, in particular ozonized olive oil and liquid vegetable extracts, for the topical treatment of vaginosis and/or vulvovaginitis of bacterial and/or fungal origin.

7 Claims, No Drawings

(56) References Cited

FOREIGN PATENT DOCUMENTS

WO      2012168770      12/2012

OTHER PUBLICATIONS

Berenji, et al., "Comparing the Effect of Ozonized Olive Oil with Clotrimazole on Three *Candida* Species *C. albiacans*, *C. glabrata*, *C. krusei*", E3 Journal of Microbiology Research, vol. 2(1), pp. 009-013, Jan. 2014.

Diaz, et al., "Comparative Study of Ozonized Olive Oil and Ozonized Sunflower Oil", J. Braz. Chem. Soc., vol. 17, No. 2, pp. 403-407, 2006.

Bulent, "Ozonated olive oils and the troubles", Journal of Intercultural Ethnopharmacology, Apr.-Jun. 2014, vol. 3, Issue 2.

Gomez, et al., "Chemical Analysis of Ozonized Theobroma Fat", JAOCS, vol. 83, No. 11, 2006, pp. 943-946.

Kogawa, et al., "Synthesis, Characterization, Thermal Behavior, and Biological Activity of Ozonides from Vegetable Oils", The Royal Society of Chemistry, 2013, pp. 1-13.

Kumar, et al. "Efficacy of Ozonized Olive Oil in the Management of Oral Lesions and Conditions: A Clinical Trial", Contemporary Clinical Dentistry, 2016, 11 pages.

Moureu, et al., "Ozonation of Sunflower Oils: Impact of Experiemental Conditions on the Composition and the Antibacterial Activity of Ozonized Oils", Chemistry and Physics of Lipids, vol. 186, Feb. 2015, pp. 79-85 (Abstract).

Tellez, et al., "Measurement of Peroxidic Species in Ozonized Sunflower Oil", The Journal of the International Ozone Association, vol. 28, Issue 3, 2006 (Abstract).

International Preliminary Report on Patentability for PCT/IB2018/052324 dated Oct. 8, 2019, 7 pages.

International Preliminary Report on Patentability for PCT/IB2018/059205 dated Mar. 5, 2020, 14 pages.

International Search Report for PCT/IB2018/052324 dated Jun. 20, 2018, 4 pages.

International Search Report for PCT/IB2018/059205 dated Mar. 21, 2019, 4 pages.

Written Opinion for PCT/IB2018/052324 dated Oct. 11, 2018, 6 pages.

Written Opinion for PCT/IB2018/059205 dated May 31, 2019, 6 pages.

D'Auria et al., "Antifungal activity of Lavandula angustifolia essential oil against *Candida albicans* yeast and mycelial form", Medical Mycology, Aug. 2005, 43, 391-396.

Japanese Office Action; Application No. 2020-528966; dated Aug. 12, 2022; 11 pgs.

Nozaki, et al., "Antifungal Activity of Essential Oils and Their Constituents against *Candida* Spp. and Their Effects on Activity of Amphotericin B"; The Pharmaceutical Society of Japan; vol. 130; 2010; pp. 895-902.

Gazim, et al., "Antifungal Activity of the Essential Oil from *Calendula officinalis* L. (Asteraceae) Growing in Brazil"; Brazilian Journal of Microbiology; 2008, pp. 61-63.

Herman, "Essential Oils and Herbal Extracts as Antimicrobial Agents in Cosmetic Emulsion"; Indian J. Microbial; Apr.-Jun. 2013; pp. 232-237.

Bona, et al., "Sensitivity of *Candida albicans* to Essential Oils: Are they an Alternative to Antifungal Agents?"; Journal of Applied Microbiology; ISSN 1364-5072; pp. 1530-1545.

Japanese Office Action; Application No. 2020-504464; dated Sep. 13, 2022; 11 pgs.

Australian Examination Report; Application No. 2018248728; dated Jul. 4, 2023; 3 pgs.

\* cited by examiner

NATURAL COMPOSITION FOR USE IN GYNECOLOGY

PRIORITY CLAIM

This application is a continuation of U.S. patent application Ser. No. 16/500,926 filed Oct. 4, 2019, which is a 371 of PCT Patent Application No. PCT/IB2018/052324 filed Apr. 4, 2018, which claims priority to Italian Patent Application No. 102017000037319 filed Apr. 5, 2017, each of which is incorporated by reference as if fully set forth herein.

DESCRIPTION

Technical Field

The present invention relates to a composition based on components of natural origin for the topical treatment of vulvovaginitis of bacterial and/or fungal origin.

Prior Art

Genital tract infections represent a recurrent problem for the female population and constitute the highest percentage of the causes inducing women to request a gynaecologist's advice. Vulvovaginitis is one of the most common infections of the female genital tract. For women, vulvovaginitis can become an extremely invalidating pathology, both due to the frequency at which the infection manifests itself, and its tendency to relapse, which often becomes a source of both psychological distress and physical discomfort, as well as the possible complications, some of which also potentially very serious.

Furthermore, given the widespread nature of this pathology, the treatment of female genital tract infections represent a major item of expenditure for the health system. Bacterial vaginosis and vaginitis caused by *Candida albicans* globally account for about 90% of the acute and/or chronic inflammations of the female genital tract. Bacterial vaginosis is a more common condition than candidiasis or *Trichomonas* infections and today represents about 40-50% of all cases of vaginitis. Bacterial vaginosis is often associated with post-partum endometritis, an increase in the risk of postoperative infections, inflammatory pelvic disease, increase in miscarriages, premature rupture of uterine membranes and increased risk of infections associated with sexually transmitted diseases. Bacterial vaginosis is characterised by excessive vaginal secretion with a foul odour in the symptomatic forms, whilst non-symptomatic bacterial vaginosis is present in 50% of women.

Women who are not treated generally show a remission in about 30% of cases. At present the recommended treatments for bacterial vaginosis in unpregnant symptomatic women include administration by mouth or via vaginal suppositories containing metronidazole or clindamycin. The standard treatment with metronidazole has a curative efficiency, with a disappearance of symptoms, in about 70-80% of the cases analysed after a month of treatment, associated with a risk of relapse in 33% of women at 3 months and approximately between 49% and the 66% one year after the initial infection.

Furthermore, in 10-20% of cases, metronidazole has negative secondary effects including secondary vaginal infections caused by *Candida* spp. Vulvovaginal candidiasis is defined as symptomatic vaginitis caused by infection by the fungal species *Candida* ssp. Candidiasis is commonly defined as recurrent when four or more symptomatic episodes occur in one year. Vaginal candidiasis is estimated to be the second most common cause of vaginal infection after bacterial vaginosis. Asymptomatic *Candida* infections show a prevalence of 10% in women with an ascertained diagnosis, whereas about 72% of women show the presence of at least one undiagnosed *Candida* infection. Infection by *Candida albicans* is the etiopathological cause of candidiasis in 85%-90% of cases.

Intravaginal treatment with antifungal and/or antibiotic drugs containing synthetic active ingredients certainly represents an effective approach for eradicating infection in the acute phase. However, relapses and the manifestation of side effects due to the use of these drugs are not infrequent. Thus, there remains a felt need in this field to have products for the topical treatment of vulvovaginitis of fungal and/or bacterial origin, which, the therapeutic effect being equal, show a lower risk of side effects than drugs bases on synthetic active ingredients associated with a smaller likelihood of relapse of the infection due to the development of drug-resistant colonies.

With respect to the possibility of using remedies that are not of pharmacological origin, *calendula* may be mentioned as a recommended phytotherapeutic remedy. *Calendula* is recommended by virtue of its antimicrobial and antiseptic properties both against bacteria and fungi. For relapsing disorders, another possible phytotherapeutic remedy is *Melaleuca altemifolia*. As phytotherapeutic remedies for treating *Candida albicans* infections (cystitis), also solely in case of inflammation, recourse is had to remedies with an antiseptic and anti-inflammatory action, such as bilberry and grapefruit (seeds).

As regards both treatments with antibiotic drugs and the remedies of phytotherapeutic origin mentioned above, the main risks tied to their administration are related to hypersensitivity to the active principle or to the substance. In the case of antibiotics, a further problem for the treatment of vaginal infections lies in induced drug resistance and thus the high risk of relapsing infections, which in some cases can even become chronic. The incidence of relapses is 33% at 3 months and approximately between 49% and 66% at one year after the initial infection with a treatment based on metronidazole (Bradshaw CS, et al., JID. 2006; 193:1478-87; Sobel J D et al., *Am J Obs Gyne*. 2006; 194:1283-9). The effectiveness of ozonised vegetable oils, in particular of ozonized olive oil, in the treatment of fungal infections caused by *C.albicans* has recently been studied. Geweely N. verified that ozonized olive oil (oleozone) with a peroxide value (PV) of 1 o 500-800 mmol/Kg, obtained by bubbling ozone through pure olive oil for eight weeks, is effective in reducing the growth of various fungi, including *C.albicans*. The best results in terms of antimicrobial activity were obtained with an oleozone with a PV of 650 (Int. J. Agri. Biol., Vol. 8, No. 5, 2006, 670-675). Berenji F. et al. confirmed that completely ozonized olive oil inhibits the proliferation 1 s in vitro of various strains of *Candida*, including *C.albicans* (E3 Journal of Microbiology Research Vol. 2(1), p.009-013, 2014). The ozonized olive oil was obtained by bubbling ozone through the oil for three weeks. Schwartz A. studied the effects of the topical application of ozone, both in the form of a gas and in the form of ozonized olive oil 400-600 PV, on patients who had been affected by vulvovaginitis caused by *C.albicans* tor at least 6 months, which showed drug resistance. The combined administration of ozone gas and 1 ml/die of ozonized olive oil led 85% of positive responses to the treatment. Moreover, 10% of the patients did not report any relapse after 12 months (Revista Espanola de Ozoneterapia, Vol. 5, No. 1, 2015, 99-107).

Although the antifungal effectiveness of ozonized olive oil against *C.albicans* infections is known, the peroxide value of the tested oils is rather high, and the oil can be irritating to the vaginal mucosa in prolonged treatments. In this context, the main task of the present invention is to propose a composition for the topical treatment of vaginosis and/or vulvovaginitis, which is highly effective both in the short and long terms, not irritating to the vaginal epithelium and not so cytotoxic as to alter the vaginal microenvironment and put it into dysbiosis. A further technical task of the present invention is to provide a composition capable of decreasing the bacterial load of the pathogenic agents which limits its antibacterial and/or antifungal action to the physiological flora of the vaginal mucosa.

SUMMARY

In a first aspect, the present invention relates to an ozonized olive oil having a peroxide value of 50-350 mEq $O_2$/Kg comprising at least one liquid vegetable extract selected from among *Allium* spp., *Aloe* spp., *Calendula officinalis*, *Cinnamomum* spp., *Curcuma* spp., Lavender spp., *Melaleuca* spp., *Plantago*, *Salvia officinalis*, *Salvia miltiorrhiza*, *Thymus* spp., *Zingiber* spp. and mixtures thereof. In a further aspect thereof, the present invention relates to an ozonized olive oil as described above for gynaecological use, in particular for use in the topical treatment of bacterial and/or fungal vaginosis and/or vulvovaginitis.

The Applicant has found, wholly unexpectedly, that an ozonized olive oil with the specified peroxide value and comprising the above-described components has a high effectiveness associated with a fast rate of action when used in the topical treatment of vaginosis and/or vulvovaginitis of bacterial and/or fungal origin, in particular due to infections caused by *Candida albicans*, *Candida glabrata* and/or *Gardnerella vagina/is*. The ozonized olive oil as described above has proven not to be irritating to the vaginal mucosa. Furthermore, the inhibition of the growth of the normal bacterial flora of the vaginal canal, represented, for example, by Lactobacilli, is only marginally influenced by the treatment with the ozonized olive oil according to the invention, thus enabling a rapid rebalancing of physiological conditions following a topical treatment.

Further advantages of the present invention will become apparent from the detailed description that follows and from the examples, which, however, have only a non-limiting demonstrative purpose.

DETAILED DESCRIPTION

In the context of the present invention the percentages are to be understood as expressed by weight, unless otherwise specified.

In the context of the present invention, the term "microbial" is synonymous of bacterial and/or fungal.

In a first aspect, the present invention relates to an ozonized olive oil having a peroxide value of 50-350 mEq $O_2$/Kg comprising at least one liquid vegetable extract selected from among *Allium* spp., *Aloe* spp., *Calendula officinalis*, *Cinnamomum* spp., *Curcuma* spp., Lavender spp., *Melaleuca* spp., *Plantago*, *Salvia officinalis*, *Salvia* miltiorrhiza, *Thymus* spp., *Zingiber* spp. and mixtures thereof.

In one embodiment, the ozonized olive oil according to the invention can comprise 0.5-10.0% by weight of at least one liquid vegetable extract selected from among *Allium* spp., *Aloe* spp., *Calendula officinalis*, *Cinnamomum* spp., *Curcuma* spp., Lavender spp., *Melaleuca* spp., *Plantago*, *Salvia officinalis*, *Salvia* miltiorrhiza, *Thymus* spp., *Zingiber* spp. and mixtures thereof, said percentage representing the total weight of the at least one liquid vegetable extract relative to the total weight of the mixture.

According to one embodiment, the ozonized olive oil according to the invention can comprise or consist of: (a) 0.5-10.0% by weight of at least one liquid vegetable extract selected from among *Allium* spp., *Aloe* spp., *Calendula officinalis*, *Cinnamomum* spp., *Curcuma* spp., Lavender spp., *Melaleuca* spp., *Plantago*, *Salvia officinalis*, *Salvia* miltiorrhiza, *Thymus* spp., *Zingiber* spp. and mixtures thereof; and (b) 90.0-99.5% by weight of ozonized olive oil having a peroxide value of about 50-350 mEq $O_2$/Kg.

The at least one liquid vegetable extract of *Allium* spp. can be selected from among a liquid vegetable extract of *Allium cepa* L., *Allium sativum* and mixtures thereof. The at least one liquid vegetable extract of *Melaleuca* spp. can be selected from among a liquid vegetable extract of *Melaleuca leucadendra*, *Melaleuca cajuputi*, *Melaleuca alternifolia* and mixtures thereof.

The at least one liquid vegetable extract of *Thymus* spp. can be selected from among a liquid vegetable extract of *Thymus vulgaris*, *Thymus leucotrichus*, *Thymus serpillum* and mixtures thereof. In one embodiment, the at least one liquid vegetable extract can be selected from among an alcohol extract, glycerine extract, glycol extract, oil-based extract, essential oil and mixtures thereof, preferably the at least one liquid vegetable extract can be at least one essential oil. Preferably, the at least one liquid vegetable extract can be at least one essential oil selected from among *Allium* spp., *Aloe* spp., *Calendula officinalis*, *Cinnamomum* spp., *Curcuma* spp., Lavender spp., *Melaleuca* spp., *Plantago*, *Salvia officinalis*, *Salvia miltiorrhiza*, *Thymus* spp., *Zingiber* spp. and mixtures thereof, more preferably it can be lavender essential oil.

The Applicant has surprisingly found that, besides imparting in some cases a particularly pleasant fragrance to the composition, the presence of the at least one liquid vegetable extract in the ozonized olive oil according to the invention positively influences the rate of action and/or the effectiveness of the oil itself in the treatment of vaginal infections, by enhancing the antifungal and/or antibacterial effect in the short term.

In one embodiment, the ozonized olive oil according to the invention can comprise 0.5-2.5% by weight of liquid vegetable extract of Lavender spp., preferably of essential oil of Lavender spp., According to one variant, the ozonized olive oil according to the invention can comprise or consist of: (a) 0.5-2.5% by weight of liquid vegetable extract of Lavender spp., preferably of essential oil of Lavender spp.; and (b) 97.5-99.5% by weight of ozonized olive oil having a peroxide value of about 50-350 mEq $O_2$/Kg.

In a further embodiment, the ozonized olive oil having a peroxide value of 50-350 mEq $O_2$/Kg can comprise a mixture of liquid vegetable extracts, preferably of essential oils, of Lavender spp., *Calendula officinalis* and *Melaleuca* spp., in a total amount of about 1.0-3.0% by weight, preferably about 1.0-2.5% by weight.

In one embodiment, the ozonized oil according to the invention can comprise or consist of: (a) 1.0-3.0% by weight, preferably 1.0-2.5% by weight, of a mixture of liquid vegetable extracts, preferably of essential oils, of Lavender spp., *Calendula officinalis* and *Melaleuca* spp; and (b) 97.0-99.0% by weight, preferably 97.5-99.0% by weight, of ozonized olive oil having a peroxide value of about 50-350 mEq $O_2$/Kg.

In one embodiment, the ozonized olive oil can have a peroxide value of about 100-350 mEq $O_2$/Kg, preferably about 150-350 mEq $O_2$/Kg, more preferably about 250-350 mEq $O_2$/Kg. The peroxide value (also indicated as PV) represents the amount of peroxides present in an ozonized oil and is expressed as milliequivalents of active oxygen contained in 1000 g of oil. This value is determined according to the method described below.

The ozonized olive oil can be obtained by bubbling a gaseous mixture comprising ozone through olive oil for a time that is sufficient to enable the reaction of the ozone with the double bonds present in the unsaturated fatty acids contained in the olive oil. In order to obtain the ozonized olive oil useful for the implementation of the present invention, use can be made of different ozonization processes which are in themselves known to the person skilled in the art, such as, for example the process disclosed in patent application EP2025740A1, the entire contents of which are incorporated herein by reference.

The olive oil ozonization reaction can be conducted under conditions suitable for obtaining an ozonized olive oil with a peroxide value comprised in the range specified above or, preferably, it can be conducted until obtaining a complete ozonization of the oil, which generally leads to an ozonized oil with a peroxide value greater than 350 mEq $O_2$/Kg, which can subsequently be diluted with non-ozonized olive oil (virgin olive oil) until obtaining the desired peroxide value.

As the ozonized olive oil of the present invention can be used in the treatment of fungal and/or bacterial vaginosis and/or vulvovaginitis, the oil ozonization reaction can advantageously take place in apparatus able to ensure an extremely low level of microbiological contamination, compatible with the standards provided under legislation regarding the placing on the market of drugs and/or medical devices.

In a preferred embodiment, the olive oil usable as a raw material in the production of the ozonized olive oil can be a refined or organic olive oil. In the context of the present invention, organic olive oil means an olive oil produced in accordance with the provisions of Regulation (EC) No. 834/2007 and subsequent amendments, as well as the associated implementing regulations.

Organic olive oil is a raw material that makes it possible to obtain an ozonized olive oil free of residues of synthetic chemical compounds, which, as such or as a result of the ozonisation reaction, could cause adverse effects during the topical application of the ozonized oil itself on the vaginal mucosa.

In one embodiment, the olive oil usable as a raw material in the production of the ozonized olive oil according to the invention can have at least one of the following characteristics:
 density at 20° C.: 0.90-0.95 g/ml; and/or
 peroxide value: 20 mEq $O_2$/Kg, preferably 10 mEq $O_2$/Kg; and/or
 acid value: 2.0 mg KOH/g, preferably 1.6 mg KOH/g.

In a preferred embodiment, the olive oil usable as a raw material can have all of the characteristics set forth above. The ozonized olive oil according to the invention can be obtained by mixing an ozonized olive oil and at least one liquid vegetable extract as described above, in any order, preferably at ambient temperature and pressure (around 25° C. and 1 atm.), under stirring, using methods and apparatus normally used in the art to obtain mixtures. The ozonized olive oil of the invention appears as pale yellow oily ointment, whose odor may be strongly influenced by the nature of the at least one liquid vegetable extract comprised in the oil.

The Applicant has surprisingly found that the ozonized olive oil comprising at least one liquid vegetable extract as described above is effective in inhibiting bacterial and/or fungal proliferation, in particular in inhibiting the proliferation of *Candida albicans* and/or *Gardenerella vagina*/is, which are responsible for nearly the totality of cases of vaginosis and/or vulvovaginitis, without inhibiting the proliferation of non-pathogenic species of the vaginal microenvironment. The ozonized oil according to the invention is further characterized by a high rapidity of action against bacterial and/or fungal infections and, moreover, the effect of inhibiting bacterial and/or fungal proliferation lasts for a long time, even up to 24 h. This characteristic is particularly advantageous for the topical treatment of microbial infections of the vaginal mucosa, since the ozonized oil according to the invention is capable of exerting its antibacterial and/or antifungal activity for up to 24 h after its application, thus well beyond the duration of its presence in the vaginal canal.

Advantageously, the ozonized olive oil according to the invention, comprising at least one liquid vegetable extract as described above, exhibits an extremely low activity in inhibiting the growth of the bacterial flora normally present under physiological conditions in the vaginal canal. Furthermore, the ozonized olive oil according to the invention has low irritating potential when applied topically on the vaginal mucosa. The presence of the above-described liquid vegetable extracts lends the ozonized oil according to the invention greater rapidity of action in inhibiting microbial growth, preferably fungal growth, in particular for an ozonized oil with a low peroxide value.

Therefore, in a further aspect thereof, the present invention relates to the gynaecological use of an ozonized oil as described above, in particular in the topical treatment of bacterial and/or fungal vaginosis and/or vulvovaginitis, even more specifically in the topical treatment of vulvovaginitis caused by at least one pathogen selected from among fungi belonging to the genus *Candida* and *Gardnerella vagina*/is. In one embodiment, the present invention relates to the use of an ozonized oil as described above for the topical treatment of vulvovaginitis caused by at least one pathogen selected from among *Candida albicans, Candida glabrata* and *Gardnerella vagina*/is.

In a further aspect thereof, the present invention relates to an ozonized oil as described above for gynaecological use, preferably for use in the topical treatment of bacterial and/or fungal vaginosis and/or vulvovaginitis, even more preferably for use in the topical treatment of vulvovaginitis caused by at least one pathogen selected from among fungi belonging to the genus *Candida* and *Gardnerella* vagina/is. In one embodiment, the present invention relates to an ozonized oil for use in the topical treatment of vulvovaginitis caused by at least one pathogen selected from among *Candida albicans, Candida glabrata* and *Gardnerella* vagina/is.

In one embodiment, the ozonized oil for gynaecological use, preferably for use in the topical treatment of bacterial and/or fungal vulvovaginitis, can comprise applying inside the vagina a pharmacologically effective amount of said ozonized olive oil as described above, preferably it can comprise applying inside the vaginal cavity vaginal about 1-20 ml/die, more preferably about 3-10 ml/die, of said ozonized olive oil.

In one embodiment, the gynaecological use of the ozonized olive oil can comprise applying inside the vaginal cavity the ozonized olive oil as described above, for at least 3 days, preferably for 3-6 days, every other day, i.e. with intervals of about 48 hours between one administration and the other, for at least two administrations, preferably for at least 3 administrations, preferably, but not exclusively, in the daily dose indicated above.

This therapeutic protocol is indicated in the treatment of non-recurring, non-relapsing bacterial and/or fungal vaginosis and/or vaginitis. In a further embodiment, the gynaecological use of the ozonized olive oil as described above can comprise applying inside the vaginal cavity said ozonized olive oil for a period of at least 10 days, preferably for 10-20 days with 72-hour intervals between one application and the other, preferably, but not exclusively, in the daily dose indicated above. This therapeutic protocol is particularly useful in the treatment of relapsing or chronic, also drug-resistant, bacterial and/or fungal vulvovaginitis.

In a further aspect, the present invention relates to a pharmaceutical composition comprising the ozonized olive oil according to the invention as described above and at least one pharmacologically acceptable excipient.

In one embodiment, said pharmaceutical composition can be in the form of an ointment, cream, gel, foam, emulsion or solution (e.g. vaginal douche) and can be prepared by mixing the components by means of processes and apparatus which are in themselves known in the art.

In a further aspect, the present invention relates to a medical device comprising the ozonized olive oil according to the invention or the pharmaceutical composition, as described above. In the context of the present invention, medical device means a device as defined in Directive 93/42/EEC. Preferably, the medical device can be selected from among an instrument, apparatus or composition. The medical device can comprise the ozonized olive oil according to the invention and at least one pharmacologically acceptable excipient.

In one embodiment, the medical device according to the invention can be a composition, preferably said composition being selected from among an ointment, cream, gel, foam, emulsion or solution (e.g. vaginal douche).

In a preferred embodiment, the medical device can be a single-use medical device, preferably comprising an ointment or a cream.

By virtue of the high rapidity of action of the ozonized oil according to the invention against bacterial and/or fungal infections, as well as the long-lasting effect of said oil in inhibiting bacterial and/or fungal proliferation, advantageously, the risk of microbial contamination of the medical device according to the invention is extremely low, also in the event of accidental contact with pathogenic microorganisms due, for example, to an incorrect use of the device itself. The pharmaceutical composition or medical device comprising the ozonized olive oil according to the present invention can be used as previously described.

The examples that follow have solely a non-limiting illustrative character.

Methods

Determination of the peroxide value (PV): iodometric titration with sodium thiosulphate of the iodine liberated by the reaction of the peroxides with potassium iodide (compliant with AOAC method No. 28.022). Apparatus: Mettler Toledo G20 titrator provided with an internal burette and DMi147-SC combined electrode (platinum—pH) and LabX® titration software. Titrating solution: sodium thiosulphate 0.1N (EXAXOL, Italy). Prepare a solution ("Sol.A") by mixing glacial acetic acid (#Cat.33209, SIGMA Aldrich) and chloroform (#Cat.132950-1L, SIGMA Aldrich) in a proportion of 3:2 v/v, under gentle stirring. Before taking the measurement, remove the electrode from the liquid it is preserved in and wash the electrode with deionised water for a few seconds. Weigh about 4 g of potassium iodide (#Cat.30315, SIGMA Aldrich) into the beaker of the titrator; add 30 ml of "Sol.A" under stirring. Set the timer of the instrument to 4 minutes and start it, maintaining the solution under stirring.

After 3 min. and 35" have elapsed, add 25 ml of deionised water to the solution and proceed with the automatic determination of the blank value (in the absence of the sample) with sodium thiosulphate. The blank determination makes it possible to calculate the relative error in the peroxide value due to changes in potential caused by the presence of any impurities in the reagents. The value in mmol of the titrant used for blank determination is memorised by the instrument as 8[1]. To determine the peroxide value of the sample, exactly weigh about 2 g of sample into the beaker of the titrator, recording the amount of sample weighed (p) on the instrument, add 30 ml of "Sol.A" and stir until the sample is completely dissolved. Add about 4 g of K1 to the solution to be titrated, set the timer of the instrument to 4 minutes and start it, maintaining the solution under stirring. After 3 min. and 35" have elapsed, add 25 ml of deionised water to the solution and proceed with the automatic titration of the iodine liberated from the sample with sodium thiosulphate. The result of the titration is positive if the instrument is able to record a minimum of 11 points on which to build the curve mapping the changes in potential and identify the curve inflection point.

The instrument directly provides the peroxide value in meq/Kg 02. The peroxide value is calculated as the arithmetic mean of three measurements performed on the same sample. Wash the electrode with chloroform between measurements. Acid value: AOCS method Cd3d-63.

Microbial plate count: 1 g of the sample on which the plate count will be carried out is withdrawn and diluted up to $1\times10^6$ times with a pH 7 solution of sodium chloride—peptone containing the most common preservative neutralising agents (polysorbate 80, soy lecithin, L-histidine). The diluted sample is subsequently plated in Petri plates containing the selective agarised culture medium (Casein *soya* bean digest *agar* tor the bacteria and *Sobouraud* glucose *agar* tor the fungi). The plates are incubated in a temperature-controlled environment at 34±1° C. in the case of bacteria and at 22±1° C. in the case of fungi and moulds, for a long enough time to enable sufficient growth of the microorganisms for the purpose of the count (18-24 h for bacteria, 3-7 days for yeasts and moulds). A determination is made of the number of colony-forming units per gram of sample (CFU/g) and the value of the number of colonies observed is corrected by the dilution factor.

Example 1

About 5 litres of an organic olive oil having the characteristics shown in Table 1 was loaded into a discontinuous reactor and ozonized by bubbling dry air containing about 3 vol. % of ozone (generated on site by an ozone generator) into the oil. The reaction was conducted at a temperature of 10-15° C. and pressure of 70-90 kPa, for about 36 hours, using an ozone flow rate of 40 g/h. The olive oil obtained was completely ozonized, with a PV of 430 mEq $O_2$/Kg (hereinafter referred to as "oil PV430"), and appeared as a yellow oily liquid.

The oil PV430 was subsequently diluted with the olive oil used as a raw material in the ozonization reaction until obtaining an ozonized olive oil with a PV of 299 mEq0$_2$/Kg (mean value obtained out of three measurements, hereinafter referred to as "oil PV300").

Organic lavender essential oil was subsequently added to the oil PV300 in a final concentration of 2% by weight relative to the total weight of the olive oil and essential oil mixture.

All the processes were carried out in a negative pressure environment with a filtered air supply to ensure adequate conditions of sterility.

TABLE 1

Characteristics of virgin olive oil

| | |
|---|---|
| CAS Number | 8001-25-0 |
| Appearance | Liquid |
| Density at 20° C. | 0.9-0.95 q/ml |
| Peroxide value | 20 mEQO2/Kq |
| Acid value | 1.6 mq KOH/q |
| Unsaponifiables | 2% |
| C16:0 | 7.5-20% |
| C16:1 | 3.5% |
| C18:0 | 0.5-5% |
| C18:1 | 56-85% |
| C18:2 | 3.5-20% |
| C18:3 | 1% |
| :::: C20:0 | 1% |

A plate count of microorganisms was performed on a sample of oil PV300 containing lavender essential oil. The results are shown in Table 2.

TABLE 2

Microbial plate count on oil PV300 containing lavender essential oil

| | CFU/g |
|---|---|
| Total mesophilic bacterial load | <10 |
| Yeasts and moulds | <10 |

Example 2

The oil PV300 containing lavender essential oil produced in Example 1 was tested in order to assess its antibacterial and antifungal properties vis-a-vis the strains relevant for the intended use (topical treatment of vaginosis and/or vulvovaginitis): G. vagina/is and C. albicans.

Furthermore, in order to verify the lack of influence on the bacterial flora normally present in the vaginal canal under physiological conditions, the activity vis-a-vis L. acidophilus was also investigated.

The strains of G. vagina/is, C. albicans and L. acidophilus used for the test were prepared by thawing an aliquot of each strain frozen at −30° C., reconstituted in liquid medium, isolated and then allowed to grow by incubating the strains under the culture conditions indicated in Table 3. Each strain was inoculated into a surface layer of agar at the concentration indicated in Table 3; the concentration of viable cells was determined by means of the plate count method.

TABLE 3

| STRAIN | CULTURE CONDITIONS | NOCULUM (CFU/q) |
|---|---|---|
| Gardnerella vagina/is | Gasman Agar Base (2-3 days - 37° C. - | $3.3 \times 10^4$ |
| Candida albicans ATCC 10231 | bauraud-dextrase agar (3-4 days - 22° C.) | $8.0 \times 10^3$ |
| Lactobacillus acidophilus ATCC 4356 | de Man, Ragasa a Sharpe agar (3-4 days - 37° C.- anaerabiasis) | $3.9 \times 10^4$ |

Some samples of the oil PV300 containing lavender essential oil produced in Example 1 were tested as such by depositing them on 25 mm cellulose disks until the oil was completely absorbed. The disks were then rested on the layer of inoculated agar. The inhibition of microbial growth was assessed after a contact time of 60 minutes by visually analysing the plates through a magnifying glass and evaluating the percentage reduction of microbial growth compared to a control zone around the covered zone of the sample. If an inhibition halo was present, it was measured in mm. The results of the test are shown in Table 4.

TABLE 4

| STRAIN | Reduction in microbial growth | Inhibition halo |
|---|---|---|
| Gardnerella vagina/is | 100% | 0 mm |
| Candida albicans ATCC 10231 | 100% | 1 mm |
| Lactobacillus acidophilus ATCC 4356 | 47.7% | 0 mm |

The activity of the oil PV300 containing lavender essential oil in countering microbial growth is excellent in the case of the pathogenic species and shows to be slight with respect to the normally present bacterial flora.

Example 3

The potential skin irritation on the vaginal epithelium was evaluated in vitro by means of a cytotoxicity assay: cell survival test with three-dimensional vaginal epithelium reconstructed in vitro (MTT test). The three-dimensional cell model used in the test consists of 0.5 cm$^2$ diameter units of cultures of transformed human vaginal epithelial cells, maintained for 5 days in a chemically defined culture medium and in contact with air on inert polycarbonate filters. The model was purchased from Episkin® (Lyons, lot 16-HVE-015).

The ozonized oil PV300 containing lavender essential oil produced in Example 1 was applied on a sample of epithelium, in duplicate. Sodium lauryl sulphate (SLS) dissolved at 0.5% by weight in a phosphate buffer (Euroclone) was used as a positive control. The phosphate buffer was used on its own as a negative control. Exposure took place for 1 and 6 hours at about 37° C., 5% CO2. At the end of exposure, the epithelium was washed with phosphate buffer. The epithelium was incubated for 3 h at 37° C. with a 1 mg/ml solution of MTT (3-[4,5-dimethylthiazol-2-yl]-2,5-diphenyltetrazoliumbromide).

The solution was subsequently removed and replaced with isopropanol, with 2 2 s successive hours of incubation at room temperature. 2 aliquots of each epithelium were transferred into a 96-well plate for the absorbance reading, which was carried out at a wavelength of 570 nm with a Tecan Sunrise remote colorimeter, equipped with a plate reader.

Through the creation of a dose-response curve, the cytotoxicity data obtained with the MTT test (Table 5) make it possible to determine the theoretical value of ET50, that is, the time in minutes that induces a 50% reduction in cell viability in the epithelium compared to untreatedcells.

An interpretation of the result is made by comparing the ET50 of the sample with that of a mildirritant (positive control).

TABLE 5

| Sample | % mean cell viability 1 h treatment | % mean cell viability 6 h treatment | ET50 (min.) |
|---|---|---|---|
| Example 3 | 82.36 | 16.21 | 206.76 |
| Positive control | 8.26 | 6.54 | 32.70 |

The oil PV300 containing lavender essential oil of Example 1 showed no potential irritation for the human vaginal mucosa.

Examples 4-6

In order to quantitatively evaluate the effectiveness of the ozonized oil comprising lavender essential oil in countering microbial proliferation as a function of the various peroxide values, the trend in the bacterial count over time was measured in samples of ozonized oil with different values of PV, inoculated with different bacterial and fungal strains.

The oil PV430 produced in Example 1 was diluted with different percentages of organic olive oil used as a raw material in the ozonisation reaction, so as to obtain ozonized olive oil with a PV as shown in Table 6.

Lavender essential oil was subsequently mixed with each sample of oil at a final concentration of 2% by weight relative to the total weight of the olive oil/essential oil mixture.

TABLE 6

| | IP (mEq 02/Ka) |
|---|---|
| Example 4 | 299 |
| Example 5 | 119 |
| Example 6 | 64 |

Various aliquots of ozonized oil were inoculated with the following five microbial strains in the amounts shown in Tables 7-9:

*Escherichia coli* ATCC 8739
*Pseudomonas aeruginosa* ATCC 9027
*Staphylococcus aureus* ATCC 6538
*Candida albicans* ATCC 10231
*Aspergillus brasiliensis* ATCC 16404

Each inoculum was prepared by culturing the bacteria on Casein *soya* bean *agar* and the fungi on *Sabourad* glucose *agar*. The bacteria were incubated at 34±1° C. for 18-24 h, the *C. albicans* at 22±1° C. for 48 h and the *A. brasiliensis* at 22±1° C. for 5-7 days.

The concentration of the inoculum was prepared in a saline solution with a microbial load of about $10^8$ CFU/ml; the final concentration of the sample was generally comprised between $10^5$ and $10^6$ CFU/ml. At different times after inoculation and up to 24 h after inoculation, the residual microbial load for each strain was evaluated using the plate microbial count method. The results are shown in Tables 7-9.

TABLE 7

| | Example 4 (IP299) | | | | |
|---|---|---|---|---|---|
| Time | E. coli (CFU/q) | P. aeruginosa (CFU/q) | S. aureus (CFU/q) | C. albicans (CFU/q) | A. brasiliensis (CFU/q) |
| Inoculum | $5.0 \times 10$ | $4.5 \times 10^5$ | $2.3 \times 10$ | $1.9 \times 10^5$ | $3.2 \times 10^5$ |
| 0.25 h | $1.3 \times 10$ | <10 | <10 | — | — |
| 0.5 h | — | — | — | <10 | 10 |
| 2 h | <10 | <10 | <10 | — | — |
| 4 h | <10 | <10 | <10 | <10 | <10 |
| 8 h | — | — | — | <10 | <10 |
| 24 h | <10 | <10 | <10 | <10 | <10 |

TABLE 8

| | Example 5 (IP119) | | | | |
|---|---|---|---|---|---|
| Time | E. coli (CFU/q) | P. aeruginosa (CFU/q) | S. aureus (CFU/q) | C. albicans (CFU/q) | A. brasiliensis (CFU/q) |
| Inoculum | $2.3 \times 10$ | $1.0 \times 10^5$ | $2.7 \times 10^5$ | $4.0 \times 10^5$ | $2.1 \times 10^5$ |
| 0.25 h | <10 | <10 | <10 | — | — |
| 0.5 h | — | — | — | <10 | $4.0 \times 103$ |
| 2 h | <10 | <10 | <10 | — | — |
| 4 h | <10 | <10 | <10 | <10 | <10 |
| 8 h | — | — | — | <10 | <10 |
| 24 h | <10 | <10 | <10 | <10 | <10 |

TABLE 9

| | Example 6 (IP64) | | | | |
|---|---|---|---|---|---|
| Time | E. coli (CFU/q) | P. aeruginosa (CFU/q) | S. aureus (CFU/q) | C. albicans (CFU/q) | A. brasiliensis (CFU/q) |
| Inoculum | 5.0× | 4.5 × 10$^5$ | 2.3 × 10 | 1.9 × 10$^5$ | 3.2 × 10$^5$ |
| 0.25 h | 1.4× | <10 | 5.8 × 10 | — | — |
| 0.5 h | — | — | — | 3.4 × 10$^2$ | 3.0 × 10$^5$ |
| 2 h | <10 | <10 | <10 | — | — |
| 4 h | <10 | <10 | <10 | <10 | 5.0 × 10$^3$ |
| 8 h | — | — | — | <10 | <10 |
| 24 h | <10 | <10 | <10 | <10 | <10 |

The tables show that the ozonized oil comprising lavender essential oil is capable of significantly reducing the microbial load in a short space of time also with low values of PV and of maintaining this action for up to 24 hours after inoculation.

Example 7

The ozonized oil PV300 produced in example 1 was used in a pilot study at the Department of Reproductive Medicine of the Versilia Hospital (Viareggio) to verify the clinical effectiveness of the gynaecological treatment.

The study was conducted on 10 patients with recurring infections of bacterial and/or fungal origin insensitive to antibiotic treatment. The microbiological analysis on a vaginal swab showed that in 7/10 women there was a presence of infections by *Candida glabrata* and *Ureaplasma urealiticum*, whereas in the remaining 3 women the swab was positive for various bacterial and/or fungal strains.

The treatment with the ozonized oil was performed with two applications of about 5 ml of oil 72 hours apart and repeated for two weeks. At the end of the treatment in 8/10 cases a total negativazion of the vaginal swab was observed, with a recolonization by Doderlein's *bacillus* revealed by the fresh smears. In the remaining cases (2/10), relapses occurred as a result of a ping-pong infection by the partners, who showed the presence of infection by the same pathogens in the sperm culture.

What is claimed is:

1. An ozonized olive oil having a peroxide value of 50-350 mEq O$_2$/Kg, the ozonized olive oil comprising a first liquid vegetable extract from *Calendula officinalis* and a second liquid vegetable extract from *Melaleuca* spp., wherein the ozonized olive oil is in a form of an ointment, cream, gel, foam, emulsion, or solution.

2. The ozonized olive oil of claim 1, wherein the first and the second liquid vegetable extracts are together present at 0.5-10% by weight.

3. The ozonized olive oil of claim 1, wherein the first and the second liquid vegetable extracts are present in the form of essential oils.

4. The ozonized olive oil of claim 1, further comprising a third liquid vegetable extract, wherein the first, the second, and the third liquid vegetable extracts are together present at 0.5-10% by weight.

5. The ozonized olive oil of claim 1, wherein said oil has a peroxide value of 100-350 mEq O$_2$/Kg, 150-350 mEq O$_2$/Kg, or 250-350 mEq O$_2$/Kg.

6. The ozonized olive oil of claim 1, wherein the ozonized olive oil is a component of a pharmaceutical composition comprising the ozonized olive oil and at least one pharmacologically acceptable excipient.

7. The ozonized olive oil of claim 1, wherein the ozonized olive oil is in a form for medical treatment.

* * * * *